United States Patent
Yao et al.

(10) Patent No.: US 10,767,170 B2
(45) Date of Patent: Sep. 8, 2020

(54) HIGH-TEMPERATURE NEUTRAL CELLULASE AS WELL AS CODING GENE AND APPLICATION THEREOF

(71) Applicant: FEED RESEARCH INSTITUTE, CHINESE ACADEMY OF AGRICULTURAL SCIENCES, Beijing (CN)

(72) Inventors: Bin Yao, Beijing (CN); Pengjun Shi, Beijing (CN); Hong Yang, Beijing (CN); Huoqing Huang, Beijing (CN); Huiying Luo, Beijing (CN); Peilong Yang, Beijing (CN); Yaru Wang, Beijing (CN); Xiaoyun Su, Beijing (CN); Yingguo Bai, Beijing (CN); Xia Shi, Beijing (CN); Rui Ma, Beijing (CN); Kun Meng, Beijing (CN)

(73) Assignee: FEED RESEARCH INSTITUTE, CHINESE ACADEMY OF AGRICULTURAL SCIENCES, Beijing (CN)

( * ) Notice: Subject to any disclaimer, the term of this patent is extended or adjusted under 35 U.S.C. 154(b) by 532 days.

(21) Appl. No.: 15/534,491

(22) PCT Filed: Dec. 9, 2014

(86) PCT No.: PCT/CN2014/093378
§ 371 (c)(1),
(2) Date: Jun. 9, 2017

(87) PCT Pub. No.: WO2016/090556
PCT Pub. Date: Jun. 16, 2016

(65) Prior Publication Data
US 2019/0382744 A1    Dec. 19, 2019

(51) Int. Cl.
| | |
|---|---|
| *C12N 9/42* | (2006.01) |
| *C12N 1/16* | (2006.01) |
| *C12N 15/63* | (2006.01) |
| *C12R 1/85* | (2006.01) |

(52) U.S. Cl.
CPC ............. *C12N 9/2437* (2013.01); *C12N 1/16* (2013.01); *C12N 15/63* (2013.01); *C12R 1/85* (2013.01); *C12Y 302/01004* (2013.01)

(58) Field of Classification Search
None
See application file for complete search history.

(56) References Cited

FOREIGN PATENT DOCUMENTS

WO    WO2012106824 A1 *    8/2012

* cited by examiner

*Primary Examiner* — Kagnew H Gebreyesus
(74) *Attorney, Agent, or Firm* — Patshegen IP LLC; Moshe Pinchas

(57) ABSTRACT

Provided are a fungus-sourced high-temperature neutral Family-45 cullulase as well as a coding gene and application thereof. The cullulase has optimal pH value of 5.5, and optimal temperature of 60° C., has certain enzyme activity in alkaline condition, and has good alkali resistance, maintains about 70% enzyme activity in optimal condition after being processed at 90° C. for 1 hour, maintains about 50% enzyme activity in optimal condition after being processed in boiling water for 1 hour, and can be well applied in c and other fields.

14 Claims, 2 Drawing Sheets
Specification includes a Sequence Listing.

HIGH-TEMPERATURE NEUTRAL CELLULASE AS WELL AS CODING GENE AND APPLICATION THEREOF

FIELD OF THE INVENTION

The present invention relates to the field of genetic engineering, particularly to high-temperature neutral cellulase, gene and application thereof.

BACKGROUND OF THE INVENTION

Cellulose is widely found in aleurone layer and cell wall of barley, wheat, corn, rice and sorghum, a linear molecule connected by glucose through the beta-1,4-glycoside bond, accounting for about 40% of the dry weight of cells. Cellulase can be produced from a variety of microorganisms, including fungi, actinomycetes, sticky bacteria and real bacteria, and can be produced by plants. The most recent studies were focused on cellulase, which are mainly derived from fungus.

Cellulase were widely used in various industry such as food, feed, beer, medicine, textiles and bioenergy. The different industrial applications required different properties. For example, feed industry needed acidophilus cellulase, but textile industry needed high temperature and alkali cellulase. The cellulase widely used was from *Trichoderma viride*, had optimum pH value of around 5.0, and optimum temperature between 50 to 60° C., and can't meet the requirements of water washing finishing industry and paper pulp making industry because cotton fiber was tolerant to alkali but not tolerant to acid. And, thermostable cellulase will be more advantageous, since heat resistance can increase the rate of reaction, decrease the viscosity of the substrate, and inhibit the contamination of the bacteria. Therefore, it's of great significance to investigate the high-temperature neutral cellulase which is alkali resistant.

SUMMARY OF THE INVENTION

One order of the present invention is to provide a fungi-derived high-temperature neutral cellulase.

Another order of the present invention is to provide a gene coding the above high-temperature neutral cellulase.

Another order of the present invention is to provide a recombinant vector comprising the above gene.

Another order of the present invention is to provide a recombinant cell comprising the above gene.

Another order of the present invention is to provide a method of preparing above high-temperature neutral cellulase Another order of the present invention is to provide an use of the above high-temperature neutral cellulase.

Thus, in one aspect, the present invention provided a novel high-temperature neutral cellulase, CEL45, which was separated from *Thielavia arenaria* and a recombinant yeast highly expressing said cellulase.

According to an embodiment of the present invention, was provided a high-temperature neutral cellulase which is selected from:
(a) a polypeptide comprising the amino acid as shown in SEQ ID NO:1 or SEQ ID NO: 2;
(b) a polypeptide with cellulase activity which is derived from SEQ ID NO: 1 or SEQ ID NO. 2 by substitution, deletion and/or insertion of one or more amino acid residues.

SEQ ID NO. 1:
MHLSLLAPLSLLLGPVFVSAQGASGSGRTTRYWDCCKPSCAWPRKGNSPS

PVRTCDKNDNPLNDGGNTRSGCDSGGSAYTCSSQSPWAVNETVAYGWAAV

NIAGSNEAAWCCACYELTFTSGPVAGKKMVVQATNTGGDLGNNHFDIAMP

GGGVGIFNACTNQYGAPPNGWGQRYGGIGSKSECESFPEKLKAGCNWRFD

WFMGADNPDVTFRQVACPAAITAKSGCTRQNDVINETPTGPATVPTWTP*

According to the embodiment of the present invention, said cellulase comprised 249 amino acids, with a signal peptide of 20 amino acids in N-terminal, as set in forth in SEQ ID NO. 3.

SEQ ID NO. 3
mhlsllaplslllgpvfvsa

According to the embodiment of the present invention, the mature cellulase protein comprised the amino acid sequence set forth in SEQ ID NO: 2 having molecular weight of 24.2 kDa.

SEQ ID NO. 2:
QGASGSGRTTRYWDCCKPSCAWPRKGNSPSPVRTCDKNDNPLNDGGNTRS

GCDSGGSAYTCSSQSPWAVNETVAYGWAAVNIAGSNEAAWCCACYELTF

TSGPVAGKKMVVQATNTGGDLGNNHIDIAMPGGGVGIFNACTNQYGAPPN

GWGQRYGGIGSKSECESFPEKLKAGCNWRFDWFMGADNPDVTFRQVACPA

AITAKSGCTRQNDVINETPTGPATVPTWTP*

The cellulase of the present invention has high temperature tolerance, high enzyme activity in neutral condition. The cellulase of the present invention from *Thielavia arenaria*, was classified in to Family 5, and had the optimal pH value of 5.5 and the optimal temperature of 60° C., and good thermostability of maintaining about 70% of activity in the optimal condition after being processed at 60° C. for 1 h, and still about 50% of activity in the optimal condition after being processed in the boiling water for 1 h.

Yet another aspect of the invention is a gene coding the above high-temperature neutral cellulase, with the following characteristics:
(a) coding a polypeptide comprising the amino acid as shown in SEQ ID NO. 1 or SEQ ID NO. 2;
(b) coding a polypeptide with cellulase activity which is derived from SEQ ID NO: 1 or SEQ ID NO. 2 by substitution, deletion and/or insertion of one or more amino acid residues.

Preferably, the gene coding the above high-temperature neutral cellulase according to the embodiment of the present invention is selected from
(a) DNA comprising a nucleotide sequence set in forth in SEQ ID NO.4 or SEQ ID NO.5; or
(b) DNA hybridizing under stringent conditions, to a nucleotide sequence set in forth in SEQ ID NO.4 or SEQ ID NO.5, and coding polypeptide with cellulase activity.

Preferably, said gene has a nucleotide sequence set in forth in SEQ ID NO.4.

SEQ ID NO. 4 所示:
atgcacctctccctgctggccccttgtccctcctgcttggacccgtctt cgtctcggcgcagggcgcgtcgggcagcgggcggacgacgcggtactggg -continued
```
actgctgcaagccgtcgtgcgcgtggccgcgcaagggcaactcgccttcc ccggtacggacgtgcgacaagaacgacaacccgctcaacgacggcggcag cacgcgctccggctgcgacagcggcggctccgcctacatgtgctcctccc agagccctgggccgtcaacgagacggtcgcctacggctgggccgccgtc aacattgcgggctccaacgaggccgcttggtgctgtgcctgctatgagtt gacttttactagcgggccagtggcgggtaagaagatggttgtgcaggcga ctaatacgggaggggatctggggaataatcactttgatattgcggaggtg tcctccattctatttcagctgtgccgccctgatcgtgtacgtacttacat ggcgacgcccaaatagatgcccggcggtggtgtcggcattataacggcaa gaccacccagtggccgttcaaagtcagccatctgacacttcaaaaacag catgcaccaaccaatacggcgcgccgccaaacggctgggccagcgctac ggcggaatcggatccaagagcgagtgtgagagcttccccgagaagctcaa ggccggctgcaactggcgcttcgattggtatgtttccttttgtcccgcct agaggagtaatatgagctgacagcccctccaggacatgggcgccgacaa cccggacgtcaccacaggcaggtggcctgcccggccgccatcacggccaa gagcggctgcacccgccagaacgacgtcatcaacgagacgcccactgggc cgtccaccgtgcccacttggacccccgtag
```

According to an embodiment of the present invention, the gene coding cellulase isolated by PCR method, was 750 bp in length, comprising a nucleotide sequence set in forth in SEQ ID NO.6 coding a signal peptide.

```
                                            (SEQ ID NO. 6)
atgcacctctccctgctggccccccttgtccctcctgcttggacccgtctt cgtctcggcg.
```

A gene coding a mature cellulase had a nucleotide sequence set in forth in SEQ ID NO.5.

```
SEQ ID NO. 5:
cagggcgcgtcgggcagcgggcggacgacgcggtactgggactgctgcaa gccgtcgtgcgcgtggccgcgcaagggcaactcgccacccggtacggac gtgcgacaagaacgacaacccgctcaacgacggcggcaacacgcgctccg gctgcgacagcggcggctccgcctacacgtgctcctcccagagccctgg gccgtcaacgagacggtcgcctacggctgggccgccgtcaacattgcggg ctccaacgaggccgcttggtgctgtgcctgctatgagttgacttttacca gcgggccagtggcgggtaagaagatggttgtgcaggcgactaatacggga ggggatctggggaataatcactttgatattgcgatgcccggcggtggtgt cggcattttaacgcatgcaccaaccaatacggcgcgccgccaaacggct ggggccagcgctacggcggaatcggatccaagagcgagtgtgagagcttc cccgagaagctcaaggccggctgcaactggcgcttcgattggttcatggg cgccgacaaccggacgtcaccttcaggcaggtggcctgcccggccgcca tcacggccaagagcggctgcacccgccagaacgacgtcatcaacgagacg cccactgggccggccaccgtgcccacttggacccccgtag
```

The molecular mass of the mature protein is 24.2 kDa. Homology searches in GenBank were done using the BLAST server to show that the amino acid sequence (SEQ ID NO: 1) is a novel cellulase.

The present invention also provides to an isolated protein comprising the amino acid sequence depicted in SEQ ID NO: 1 or SEQ ID NO: 2. In another embodiment, the present invention relates to a derivative of said protein, which is obtainable from SEQ ID NO: 1 or SEQ ID NO: 2 by substitution, deletion and/or insertion of one or more (e.g., one or several, or a value selected from 1-10, e.g., 1, 2, 3, 4, 5, 6, 7, 8, 9 or 10, or ranges intermediated to the above-recited values) amino acid residues, and maintains the cellulase activity. For example, a common strategy is conservative amino acid substitutions that is to say, the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine). Thus, replacement with another amino acid residue from the same side chain of one or more amino acid residue would not substantially change the enzyme activity of said cellulase. Furthermore, it is well known in the art that during the cloning of genes, usually enzyme recognition sites are designed, which would result in one or several non-relating amino acid residues on the ends of target protein without affecting the activity thereof. In addition, in order to construct a fusion protein, to enhance expression of recombinant protein, to obtain an recombinant protein automatically secreted outside the host cell, or to aid in the purification of the recombinant protein, suitable peptide linker, signal peptide, leader peptide, terminal extensions, glutathione S-transferase (GST), maltose E binding protein, protein A, tags such as 6His or Flag, or proteolytic cleavage site for Factor Xa, thrombin or enterokinase are usually introduced into the N- or C-terminus of the recombinant protein or within other suitable regions in the proteins.

In another embodiment, the protein with cellulase activity according to the present invention can comprise an amino acid sequence which is coded by a nucleotide sequence which hybridizes, e.g., hybridizes under stringent conditions, to a nucleotide sequence of SEQ ID NO: 4 or SEQ ID NO:5 as set forth in the Sequence Listing. As used herein, the term "hybridizes under stringent conditions" is intended to describe conditions for hybridization and washing under which nucleotide sequences at least 60% homologous to each other typically remain hybridized to each other. Preferably, the conditions are such that sequences at least about 65%, more preferably at least about 70%, and even more preferably at least about 75% or more homologous to each other typically remain hybridized to each other. Such stringent conditions are known to one of ordinary skill in the art and can be found in Current Protocols in Molecular Biology, John Wiley & Sons, N.Y. (1989), 6.3.1-6.3.6. A preferred, non-limiting example of stringent hybridization conditions are hybridization in 6× sodium chloride/sodium citrate (SSC) at about 45° C., followed by one or more washes in 0.2×SSC, 0.1% SDS at 50-65° C. A person skilled in the art understands that high stringent condition could be realized by raising the hybridization temperature up to 50° C., 55° C., 60° C. or 65° C.

Besides, it will be appreciated by one of ordinary skill in the art that genetic polymorphism due to natural variation may exist among individuals within a population. Such natural variations can typically result in 1-5% variance in the nucleotide sequence of the cellulase gene. Any and all such nucleotide variations and resulting amino acid polymorphisms in cellulase that are the result of natural variation and that do not alter the functional activity of cellulase proteins are intended to be within the scope of the invention. Therefore, the present invention also comprised a polypeptide with cellulase activity coded by such an allele or natural variant of the polynucleotide as shown in SEQ ID NO: 4 or SEQ ID NO.5.

In a preferred embodiment, a cellulase was such a active protein that was at least about 60%, 61%, 62%, 63%, 64%, 65%, 66%, 67%, 68%, 69%, or at least about 70%, 71%, 72%, 73%, 74%, 75%, 76%, 77%, 78%, 79%, or at least about 80%, 81%, 82%, 83%, 84%, 85%, 86%, 87%, 88%, 89%, or at least about 90%, 91%, 92%, 93%, 94%, 95%, 96%, 97%, 98%, more preferably at least about 98.1%, 98.2%, 98.3%, 98.4%, 98.5%, 98.6%, 98.7%, 98.8%, 98.9%, and even more preferably at least about 99%, 99.1%, 99.2%, 99.3%, 99.4%, 99.5%, 99.6%, 99.7%, 99.8%, 99.9% or more homologous to the entire amino acid sequence as shown in SEQ ID NO: 1 or SEQ ID NO: 2 of the present invention. Ranges and identity values intermediated to the above-recited values (e.g., 60-90% homologous or 98.1-99.9% identical) are also intended to be included in the present invention.

On the other hand, the present invention provides a novel cellulase gene of SEQ ID NO: 4 or SEQ ID NO:5. The invention further encompasses nucleic acid molecules that differ from one of the nucleotide sequences depicted in SEQ ID NO: 4 or SEQ ID NO: 5 of the invention due to degeneracy of the genetic code and thus encode the same cellulase protein. In another embodiment, an isolated nucleic acid molecule of the invention is a nucleotide sequence which hybridizes, e.g., hybridizes under stringent conditions, to a nucleotide sequence of SEQ ID NO: 4 or SEQ ID NO:5, with the allele or natural variant thereof is preferred. In another embodiment, an isolated nucleic acid molecule of the invention has a nucleotide sequence encoding a protein having an amino acid sequence shown in the SEQ ID NO: 1 or SEQ ID NO:2. In a still further embodiment, the nucleic acid molecule of the invention codes a full length cellulase protein which is substantially homologous to an amino acid sequence of SEQ ID NO: 4 or SEQ ID NO: 5, for example, a protein that derived from SEQ ID NO: 1 or SEQ ID NO:2 by substitution, deletion and/or insertion of one or more (e.g., one or several, or a value selected from 1-10) amino acid residues, or one that is at least 99% homologous to the amino acid sequence of SEQ ID NO: 1 or SEQ ID NO:2. Such a nucleic acid molecule is preferably at least about 60%, 61%, 62%, 63%, 64%, 65%, 66%, 67%, 68%, 69%, or at least about 70%, 71%, 72%, 73%, 74%, 75%, 76%, 77%, 78%, 79%, or at least about 80%, 81%, 82%, 83%, 84%, 85%, 86%, 87%, 88%, 89%, more preferably at least about 90%, 91%, 92%, 93%, 94%, 95%, 96%, 97%, 97.7%, 97.8%, 97.9%, or at least about 98%, 98.1%, 98.2%, 98.3%, 98.4%, 98.5%, 98.6%, 98.7%, 98.8%, 98.9%, and even more preferably at least about 99%, 99.1%, 99.2%, 99.3%, 99.4%, 99.5%, 99.6%, 99.7%, 99.8%, 99.9% or more homologous to a nucleotide sequence of SEQ ID NO: 4 or SEQ ID NO:5. Ranges and identity values intermediate to the above-recited values (e.g., 76-97% homologous or 97.8-99.9% identical) are also intended to be included in the present invention.

In yet another embodiment, the present invention relates to a recombinant vector comprising said nucleic acid coding said cellulase, a recombinant host cell (such as *Pichia Pastoris*, yeast, and *E. coli*.) having been introduced said vector or said nucleic acid molecule, as well as a method for expressing the cellulase in a host cell. In a preferred embodiment, said cellulase gene was controlled by promoter AOXI by being inserted between sites of EcoR I and Not I in plasmid pPIC9, so as to obtain the recombinant expression vector pPIC9-cel45.

In a preferred embodiment, said recombinant host cell was strain GS115/cel45.

The present invention relates to a method of producing the said β-glucosidase, including the steps:
1) transform a host cell with the above recombinant vector, to obtain recombinant strain
2) cultivating the recombinant strain to induce to express said cellulase; and
(b) recovering and purifying the said cellulase.

The recombinant expression vectors of the invention can be designed for expression of cellulase in prokaryotic or eukaryotic cells. For example, cellulase gene can be expressed in bacterial cells such as *E. coli*, yeast such as *Pichia* or *Aspergillus*, insect cells (e.g., Sf9 cell or silkworm cell, using baculovirus expression vectors), or plant cell (such as *Arabidopsis*, tobacco, corn, and so on, mediated by *Agrobacterium tumefaciens*). Thus, the invention pertains to host cells into which a recombinant expression vector of the invention has been introduced, with *Pichia* preferred. *Pichia pastoris* is a methylotrophic yeast, capable of metabolizing methanol as its sole carbon source. This system is well-known for its ability to express high levels of heterologous proteins. As an effective expression system, many of cellulase gene have successfully expressed in *P. pastoris*. The novel cellulase gene also expressed in *P. pastoris* and had high levels of expression. So it will be very easy to mass-produce the β-glucosidase by fermentation, and the cost will be lower than ever.

Vector DNA can be introduced into prokaryotic or eukaryotic cells via conventional transformation or transfection techniques. Suitable methods for transforming or transfecting host cells can be found in Sambrook, et al. (*Molecular Cloning: A Laboratory Manual.* 2nd, ed., Cold Spring Harbor Laboratory, Cold Spring Harbor Laboratory Press, Cold Spring Harbor, N.Y., 1989), and other laboratory manuals.

A host cell of the invention, such as a prokaryotic or eukaryotic host cell in culture, can be used to produce (i.e., express) a cellulase. Accordingly, the invention further provides methods for producing cellulase proteins using the host cells of the invention. In one embodiment, the method comprises culturing the host cell of invention (into which a recombinant expression vector encoding a cellulase protein has been introduced, or into which genome has been introduced a gene encoding a wild-type or altered cellulase protein) in a suitable medium until cellulase protein is produced. In another embodiment, the method further comprises isolating cellulase proteins from the medium or the host cell. Yet another aspect of the present invention is the β-glucosidase expressed in *Pichia pastrois*. In order to ascertain the assay of the cellulase, cellulase was purified by simple approach, such as ammonium sulfate precipitation, dialysis, ultrafiltration and chromatography. After the simple purification, the purity of the cellulase was enough to study the enzyme properties.

Yet another aspect of the invention is the application of said cellulase to the textile industry and paper-making industry.

With the aim to solve the problem of lack of alkali resistance, thermostable and neutral cellulase from microorganism in the art which was suitable to textile and paper-making industry, we had isolated a novel cellulase with the characteristics: optimal pH was 5.5, optimal temperature of 60° C., alkali resistance, and good thermostability of maintaining about 70% enzyme activity in optimal condition after being processed at 90° C. for 1 hour, maintains about 50% enzyme activity in optimal condition after being processed in boiling water for 1 hour.

BRIEF DESCRIPTIONS OF THE DRAWINGS

EXAMPLES

Figure 1:
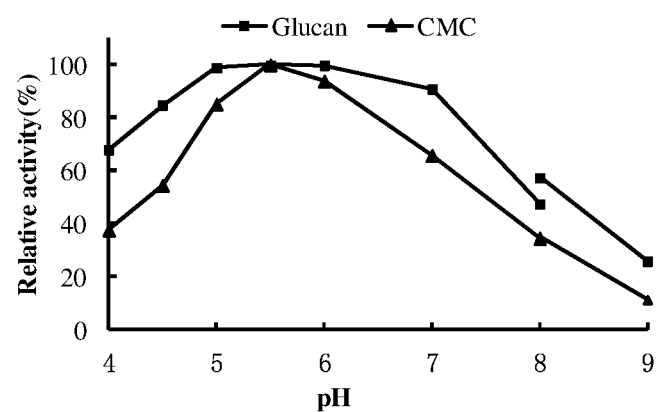
FIG. 1 shows optimum pH values for recombinant cellulase.

The present invention is further illustrated with reference to the following Examples and the appended drawings, which should by no means be construed as limitations of the present invention.

Test Materials and Reagents

1. Strains and vectors: *Thielavia arenaria* XZ7; *Pichia pastoris* strain GS115 (Invitrogen); and vector pPIC9 (Invitrogen).

2. Enzymes and other biochemical reagents: restriction endonucleases (TaKaRa); ligase (Invitrogen); and barley dextran and CMC-Na (Sigma)

3. Medium:
   (1) taking potato dextrose medium as *Thielavia arenaria* XZ7 Medium, including 1000 mL of potato juice, 10 g of dextrose, and 25 g of arga, natural pH.
   (2) *E. coli*. LB medium: 1% of peptone, 0.5% of yeast extract, and 1% of NaCl, natural pH.
   (3) BMGY medium: 1% of yeast extract; 2% of peptone; 1.34% of YNB, 0.00004% of Biotin; and 1% of glycerol (V/V).
   (4) BMMY medium: 1% of yeast extract; 2% of peptone; 1.34% of YNB, 0.00004% of Biotin; and 0.5% of methanol (V/V).

Suitable biology laboratory methods not particularly mentioned in the examples as below can be found in Sambrook, et al. (*Molecular Cloning: A Laboratory Manual.* 2nd, ed., Cold Spring Harbor Laboratory, Cold Spring Harbor Laboratory Press, Cold Spring Harbor, N.Y., 1989), and other kit laboratory manuals.

Example 1 Cloning Gene Coding Cellulase from *Thielavia arenaria* XZ7

Genomic DNA is isolated from *Thielavia arenaria* XZ7 by adding 2 mL of extract buffer mycelium, and grinding for 5 min, followed by decomposing for 120 min in a water bath at 65° C., and mixing well every 20 min, then centrifugating for 10 min at 13000 rpm at 4° C. The supernatant was extracted in phenol/chloroform to remove the impurities, followed by adding isopropanol in equal volume, settling for 30 min at −20° C., centrifugating for 10 min at 13000 rpm at 4° C. to remove supernatant, washing the precipitate with 70% ethanol twice followed by drying, dissolving in TE solution and storing at −20° C.

It was possible to design a pair of degenerate primers to amplify part fragment of the cellulase gene based on the conserved fragment of Family 45 of cellulase, GXTTRY-WDC and QFDXXIPGG

```
P1: 5'-GGYAMVACCACYCGYTAYTGGGAYTGYT-3';

P2: 5'-WCCBCCKGGRATSRMSADRTCRAAYTG-3'
```

PCR amplification was performed by optimizing PCR parameters as follows: degenerating at 94° C. for 5 minutes, followed by 30 cycles at: degenerating at 94° C. for 30 seconds/annealing temperature at 45° C. for 30 seconds/extending at 72° C. for 1 minute, and a final extension of 10 minutes at 72° C. PCR product comprising 292 bp was obtained and linked to vector pEASY-T3 for sequencing.

Based on the known fragment, the nested insertion-specific primers for TAIL PCR were designed, and named respectively as shown in table 1, wherein primer sp2 located in the downstream of primer sp1, primer sp3 located in the downstream of primer sp2, the arbitrary distance between two primer, 22~30 nt in length, and the annealing temperature at 60~65° C.

TABLE 1

Specific primers for TAIL PCR

| Primer | Sequence (5' - - - 3') | Length (bp) |
|---|---|---|
| dsp1 | CGCGCGACAAGAACGACAACCCGCTCAACGAC | 32 |
| dsp2 | CTGGGCCGCCGTCAACATTGCGGGCTCCAAC | 31 |
| usp1 | CAATGTTGACGGCGGCCCAGCCGTAGGC | 28 |
| usp2 | GTCGTTGAGCGGGTTGTCGTTCTTGTCGCGCG | 32 |

Two flanking sequences were obtained by Reverse TAIL-PCR, sequenced, and assembled into gene coding cellulase with 938 bp in full length including two introns, coding 249 amino acids and one termination codon. Said cellulase comprised a signal peptide of 20 amino acids in N-terminal, and had molecular weight of 24.2 kDa.

Example 2 Preparing Recombinant Cellulase

The coding region of mature protein was amplified. The amplification products were visualized by electrophoresis on agarose gel, and band of expected size was excised and DNA was extracted with Kit. The DNA purified was inserted into pPIC9 (Invitrogen, San Diego, Calif.) at the EcoRI and NotI sites, as described by the manufacturer instruction to obtain DNA construct pPIC-cel45. The construct was transformed into *Pichia pastoris* strain GS115 to obtain the recombinant cell GS115/cel45.

The transformed *Pichia pastoris* strain GS115 (Invitrogen) were incubated in 400 mL of BMGY for 48 h at 30° C. and 250 rpm, and then the cells were spun down and suspended in 200 mL of BMMY to induce to express cellulase. 48 hours after induction, the supernatant was recovered by spinning to test the activity of the cellulase. The recombinant β-glucosidase was expressed in *Pichia pastoris* strain GS115 as showed by SDS-PAGE.

The expression vector comprising the full-length gene coding cellulase was constructed and transformed to *Pichia*

*pastoris* strain GS115 by the same method as above, and the recombinant cellulase was also tested.

Example 3 Measuring Activity of the Recombinant Cellulase

The amount of glucose produced by hydrolyzing substrate, CMC-Na, with cellulase in 540 nm.

100 μL of diluted enzyme was mixed with 900 μL of substrate solution (1%, w/v), which was reacted at 60° C. for 10 minutes in 1M of Sodium dihydrogen phosphate-citric acid (pH 6.0). Then, 1.5 mL of DNS was added to stop the reaction. $OD_{540}$ was measured. 1 unit of enzyme activity was determined to be the enzyme amount releasing 1 μmol of glucose by decomposing substrate, for 1 minute.

Measuring the Properties of the Recombinant Cellulase Obtained in Example 2

1. Optimum pH Values and pH Stability

Figure 2:
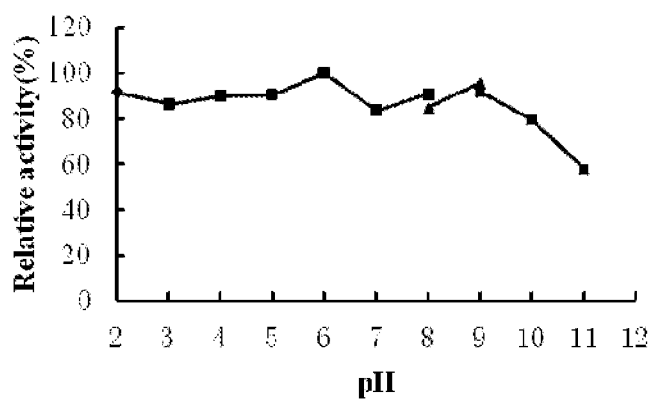
FIG. 2 shows pH stabilities for recombinant cellulase.

The cellulase purified in example 2 was reacted in the different pH to determine optimum pH. The activity of cellulase was measured with CMC-Na in 0.1M of citric acid-sodium dimetallic phosphate buffer with different pH at 60° C. As is shown in FIG. 1, the highest activity was observed at pH 5.5, more than 90% of activity was maintained in pH range of 5.0 to 7.0, and about 25% of activity was maintained at pH 9.0. FIG. 2 showed the cellulase was very stable in pH range of 2.0 to 10.0, and above 80% of activity was maintained when the cellulase was maintained at 37° C. at different pH for 60 min followed by measuring the activity in buffer with pH 4.5 at 75° C.

2. Optimum Temperature and Heat Stability

Figure 3:
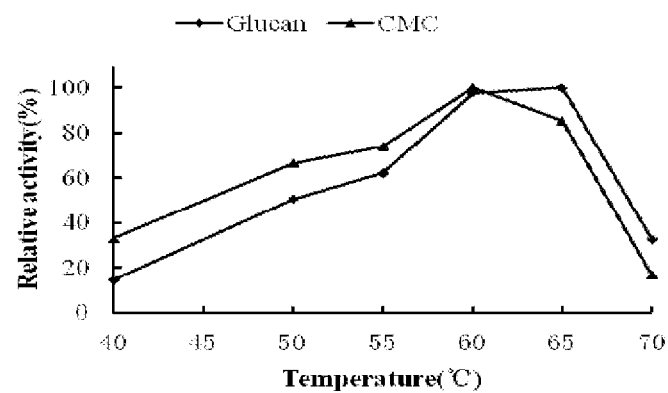
FIG. 3 shows optimum temperature values for recombinant cellulase.
Figure 4:
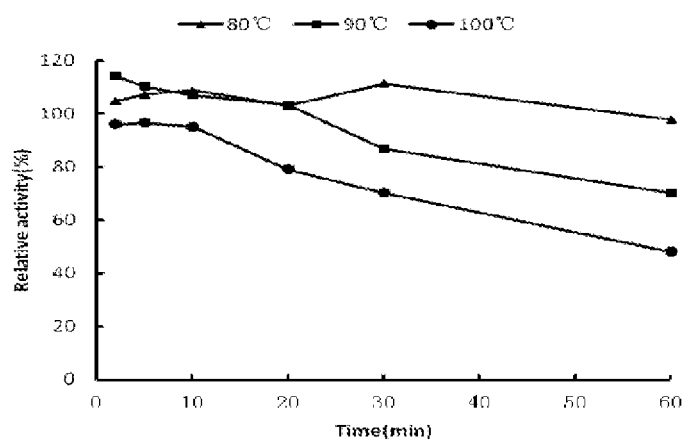
FIG. 4 shows heat stability for recombinant cellulase.

The cellulase was reacted at the different temperatures in citric acid-sodium dimetallic phosphate buffer (pH 5.5) to determine optimum temperature. The activity of cellulase was measured after being processed at different temperatures for 2, 5, 10, 20, 30, and 60 min. As shown in FIG. 3, the activity of cellulase varied with temperatures. The highest activity was observed at 60° C. FIG. 4 showed the enzyme activity was thermalstable, more than 70% of the enzyme activity was still maintained when the enzyme was maintained at 60° C. for 1 h, and about 50% of the enzyme activity was still maintained when the enzyme was maintained in boiling water for 1 h.

3. Measuring Enzyme Kinetics of Cellulase

Testing the activity of cellulase at 60° C. with the different concentration of substrate, in citric acid-sodium dimetallic phosphate buffer (pH5.5), and calculating $K_m$ as 11.28 mg/mL, and $V_{max}$ as 11256.44 μmol/min·mg when using dextran as substrate; and $K_m$ as 10.79 mg/mL, and $V_{max}$ as 1177.44 μmol/min·mg when using CMC-Na as substrate.

4. Effect of Metal Ions and Chemistry Agents on Activity of Cellulase

The effect of metal ions on cellulase activity was investigated at the pH optimum (pH 5.5) and 60° C. in a final concentration of 5 mmol/L. The result showed that, among various metal ions, the enzyme activity of cellulase almost wasn't inhibited by many metal ions, but was inhibited by $Ag^+$ and SDS. Additionally, cellulase was weakly activated by $Ca^{2+}$ and $Co^{2+}$, and obviously activated by β-mercaptoethanol.

The invention claimed is:

1. A method of degrading cellulose contained in a raw textile fiber, comprising applying a cellulase to said raw textile fiber, wherein said cellulase has the amino acid as shown in SEQ ID NO: 1 or SEQ ID NO: 2.

2. The method of claim 1, wherein said cellulase is produced by transcribing an isolated polynucleotide encoding said cellulase.

3. The method of claim 2, wherein said isolated polynucleotide has a nucleotide sequence as set in forth in SEQ ID NO.4 or SEQ ID NO.5.

4. The method of claim 3, wherein said isolated polynucleotide is in a recombinant vector.

5. The method of claim 3, wherein said isolated polynucleotide is introduced into the genome of a recombinant yeast host cell.

6. The method of claim 5, wherein said recombinant host cell is a *Pichia* cell.

7. The method of claim 1, wherein said cellulase has an optimal pH value of 5.5, the optimal temperature of 60° C., maintains about 70% of its optimal activity after incubation at 60° C. for 1 hour, and maintains 50% of its optimal activity condition after incubation in 100° C. water for 1 hour.

8. A method of degrading cellulose contained in paper pulp, comprising applying a cellulase to said paper pulp, wherein said cellulase has the amino acid sequence as shown in SEQ ID NO: 1 or SEQ ID NO: 2.

9. The method of claim 8, wherein said cellulase is produced by transcribing an isolated polynucleotide encoding said cellulase.

10. The method of claim 9, wherein said isolated polynucleotide has a nucleotide sequence as set in forth in SEQ ID NO.4 or SEQ ID NO.5.

11. The method of claim 10, wherein said isolated polynucleotide is in a recombinant vector.

12. The method of claim 10, wherein said isolated polynucleotide is introduced into the genome of a recombinant yeast host cell.

13. The method of claim 12, wherein said recombinant host cell is a *Pichia* cell.

14. The method of claim 8, wherein said cellulase has an optimal pH value of 5.5, the optimal temperature of 60° C., maintains about 70% of its optimal activity after incubation at 60° C. for 1 hour, and maintains 50% of its optimal activity condition after incubation in 100° C. water for 1 hour.

* * * * *

SEQUENCE LISTING

```
<160> NUMBER OF SEQ ID NOS: 6

<210> SEQ ID NO 1
<211> LENGTH: 249
<212> TYPE: PRT
<213> ORGANISM: Thielavia arenaria XZ7

<400> SEQUENCE: 1

Met His Leu Ser Leu Leu Ala Pro Leu Ser Leu Leu Leu Gly Pro Val
1               5                   10                  15

Phe Val Ser Ala Gln Gly Ala Ser Gly Ser Gly Arg Thr Thr Arg Tyr
            20                  25                  30

Trp Asp Cys Cys Lys Pro Ser Cys Ala Trp Pro Arg Lys Gly Asn Ser
        35                  40                  45

Pro Ser Pro Val Arg Thr Cys Asp Lys Asn Asp Asn Pro Leu Asn Asp
    50                  55                  60

Gly Gly Asn Thr Arg Ser Gly Cys Asp Ser Gly Gly Ser Ala Tyr Thr
65                  70                  75                  80

Cys Ser Ser Gln Ser Pro Trp Ala Val Asn Glu Thr Val Ala Tyr Gly
                85                  90                  95

Trp Ala Ala Val Asn Ile Ala Gly Ser Asn Glu Ala Ala Trp Cys Cys
            100                 105                 110

Ala Cys Tyr Glu Leu Thr Phe Thr Ser Gly Pro Val Ala Gly Lys Lys
        115                 120                 125

Met Val Val Gln Ala Thr Asn Thr Gly Gly Asp Leu Gly Asn Asn His
    130                 135                 140

Phe Asp Ile Ala Met Pro Gly Gly Gly Val Gly Ile Phe Asn Ala Cys
```

-continued

```
                145                 150                 155                 160
            Thr Asn Gln Tyr Gly Ala Pro Pro Asn Gly Trp Gly Gln Arg Tyr Gly
                        165                 170                 175

Gly Ile Gly Ser Lys Ser Glu Cys Glu Ser Phe Pro Glu Lys Leu Lys
                        180                 185                 190

Ala Gly Cys Asn Trp Arg Phe Asp Trp Phe Met Gly Ala Asp Asn Pro
                        195                 200                 205

Asp Val Thr Phe Arg Gln Val Ala Cys Pro Ala Ala Ile Thr Ala Lys
                        210                 215                 220

Ser Gly Cys Thr Arg Gln Asn Asp Val Ile Asn Glu Thr Pro Thr Gly
            225                 230                 235                 240

Pro Ala Thr Val Pro Thr Trp Thr Pro
                        245

<210> SEQ ID NO 2
<211> LENGTH: 229
<212> TYPE: PRT
<213> ORGANISM: Thielavia arenaria XZ7

<400> SEQUENCE: 2

Gln Gly Ala Ser Gly Ser Gly Arg Thr Thr Arg Tyr Trp Asp Cys Cys
1               5                   10                  15

Lys Pro Ser Cys Ala Trp Pro Arg Lys Gly Asn Ser Pro Ser Pro Val
            20                  25                  30

Arg Thr Cys Asp Lys Asn Asp Asn Pro Leu Asn Asp Gly Gly Asn Thr
        35                  40                  45

Arg Ser Gly Cys Asp Ser Gly Gly Ser Ala Tyr Thr Cys Ser Ser Gln
    50                  55                  60

Ser Pro Trp Ala Val Asn Glu Thr Val Ala Tyr Gly Trp Ala Ala Val
65                  70                  75                  80

Asn Ile Ala Gly Ser Asn Glu Ala Ala Trp Cys Cys Ala Cys Tyr Glu
                85                  90                  95

Leu Thr Phe Thr Ser Gly Pro Val Ala Gly Lys Lys Met Val Val Gln
            100                 105                 110

Ala Thr Asn Thr Gly Gly Asp Leu Gly Asn Asn His Phe Asp Ile Ala
        115                 120                 125

Met Pro Gly Gly Gly Val Gly Ile Phe Asn Ala Cys Thr Asn Gln Tyr
    130                 135                 140

Gly Ala Pro Pro Asn Gly Trp Gly Gln Arg Tyr Gly Gly Ile Gly Ser
145                 150                 155                 160

Lys Ser Glu Cys Glu Ser Phe Pro Glu Lys Leu Lys Ala Gly Cys Asn
                165                 170                 175

Trp Arg Phe Asp Trp Phe Met Gly Ala Asp Asn Pro Asp Val Thr Phe
            180                 185                 190

Arg Gln Val Ala Cys Pro Ala Ala Ile Thr Ala Lys Ser Gly Cys Thr
        195                 200                 205

Arg Gln Asn Asp Val Ile Asn Glu Thr Pro Thr Gly Pro Ala Thr Val
    210                 215                 220

Pro Thr Trp Thr Pro
225

<210> SEQ ID NO 3
<211> LENGTH: 20
<212> TYPE: PRT
<213> ORGANISM: Thielavia arenaria XZ7
```

<400> SEQUENCE: 3

Met His Leu Ser Leu Leu Ala Pro Leu Ser Leu Leu Gly Pro Val
1               5                   10                  15

Phe Val Ser Ala
            20

<210> SEQ ID NO 4
<211> LENGTH: 938
<212> TYPE: DNA
<213> ORGANISM: Thielavia arenaria XZ7

<400> SEQUENCE: 4

| | |
|---|---|
| atgcacctct ccctgctggc ccccttgtcc ctcctgcttg acccgtcttt cgtctcggcg | 60 |
| cagggcgcgt cgggcagcgg gcggacgacg cggtactggg actgctgcaa gccgtcgtgc | 120 |
| gcgtggccgc gcaagggcaa ctcgccttcc ccggtacgga cgtgcgacaa gaacgacaac | 180 |
| ccgctcaacg acggcggcag cacgcgctcc ggctgcgaca cggcggctc cgcctacatg | 240 |
| tgctcctccc agagcccctg gccgtcaac gagacggtcg cctacggctg gccgccgtc | 300 |
| aacattgcgg gctccaacga ggccgcttgg tgctgtgcct gctatgagtt gacttttact | 360 |
| agcgggccag tggcgggtaa gaagatggtt gtgcaggcga ctaatacggg aggggatctg | 420 |
| gggaataatc actttgatat tgcggttggt gtcctccttt tctcttttca gctgtgccgc | 480 |
| cctgtttcgt gtacgtactt acatggcgac gcccaaatag atgcccggcg gtggtgtcgg | 540 |
| cattttttaac ggcaagacct tccccttgtg gccgttcaaa gtcagccatc tgacacttca | 600 |
| aaaacagcat gcaccaacca atacggcgcg ccgccaaacg gctggggcca gcgctacggc | 660 |
| ggaatcggat ccaagagcga gtgtgagagc ttccccgaga agctcaaggc cggctgcaac | 720 |
| tggcgcttcg attggtatgt ttccttttgt ccccgcctaga ggagtaatat gagctgacag | 780 |
| ccccctccag gttcatgggc gccgacaacc cggacgtcac cttcaggcag gtggcctgcc | 840 |
| cggccgccat cacggccaag agcggctgca cccgccagaa cgacgtcatc aacgagacgc | 900 |
| ccactgggcc gtccaccgtg cccacttgga ccccgtag | 938 |

<210> SEQ ID NO 5
<211> LENGTH: 690
<212> TYPE: DNA
<213> ORGANISM: Thielavia arenaria XZ7

<400> SEQUENCE: 5

| | |
|---|---|
| cagggcgcgt cgggcagcgg gcggacgacg cggtactggg actgctgcaa gccgtcgtgc | 60 |
| gcgtggccgc gcaagggcaa ctcgccttcc ccggtacgga cgtgcgacaa gaacgacaac | 120 |
| ccgctcaacg acggcggcaa cacgcgctcc ggctgcgaca cggcggctc cgcctacacg | 180 |
| tgctcctccc agagcccctg gccgtcaac gagacggtcg cctacggctg gccgccgtc | 240 |
| aacattgcgg gctccaacga ggccgcttgg tgctgtgcct gctatgagtt gacttttacc | 300 |
| agcgggccag tggcgggtaa gaagatggtt gtgcaggcga ctaatacggg aggggatctg | 360 |
| gggaataatc actttgatat tgcgatgccc ggcggtggtg tcggcatttt taacgcatgc | 420 |
| accaaccaat acggcgcgcc gccaaacggc tggggccagc gctacggcgg aatcggatcc | 480 |
| aagagcgagt gtgagagctt ccccgagaag ctcaaggccg gctgcaactg gcgcttcgat | 540 |
| tggttcatgg gcgccgacaa cccggacgtc accttcaggc aggtggcctg cccggccgcc | 600 |
| atcacggcca gagcggctg cacccgccag aacgacgtca tcaacgagac gcccactggg | 660 |
| ccggccaccg tgcccacttg gaccccgtag | 690 |

```
<210> SEQ ID NO 6
<211> LENGTH: 60
<212> TYPE: DNA
<213> ORGANISM: Thielavia arenaria XZ7

<400> SEQUENCE: 6
atgcacctct ccctgctggc ccccttgtcc ctcctgcttg gacccgtctt cgtctcggcg    60
```